(12) United States Patent
Hasegawa et al.

(10) Patent No.: US 10,441,375 B2
(45) Date of Patent: Oct. 15, 2019

(54) MEDICAL INSTRUMENT AND ADJUSTMENT METHOD OF MEDICAL INSTRUMENT

(71) Applicant: OLYMPUS CORPORATION, Tokyo (JP)

(72) Inventors: Mitsuaki Hasegawa, Tokyo (JP); Toshihiro Yoshii, Tokyo (JP)

(73) Assignee: Olympus Corporation, Tokyo (JP)

( * ) Notice: Subject to any disclaimer, the term of this patent is extended or adjusted under 35 U.S.C. 154(b) by 383 days.

(21) Appl. No.: 15/396,913

(22) Filed: Jan. 3, 2017

(65) Prior Publication Data

US 2017/0105805 A1     Apr. 20, 2017

Related U.S. Application Data

(63) Continuation of application No. PCT/JP2015/066014, filed on Jun. 3, 2015.

(30) Foreign Application Priority Data

Jul. 10, 2014    (JP) .................................. 2014-142574

(51) Int. Cl.
*A61B 34/37*     (2016.01)
*B25J 19/00*     (2006.01)
(Continued)

(52) U.S. Cl.
CPC .............. *A61B 34/37* (2016.02); *A61B 34/30* (2016.02); *A61B 34/71* (2016.02); *B25J 3/00* (2013.01);
(Continued)

(58) Field of Classification Search
CPC ... B25J 3/00; B25J 9/065; B25J 9/1045; B25J 15/0019; A61B 34/71
See application file for complete search history.

(56) References Cited

U.S. PATENT DOCUMENTS 4,806,066 A * 2/1989 Rhodes .................... B25J 9/046
254/286
5,611,248 A * 3/1997 Peltier ...................... B25J 9/023
414/749.1
(Continued)

FOREIGN PATENT DOCUMENTS

JP    H08-019511 A    1/1996
JP    H08-286123 A    11/1996
(Continued)

OTHER PUBLICATIONS

International Search Report dated Aug. 18, 2015 issued in PCT/JP2015/066014.

(Continued)

*Primary Examiner* — David M Fenstermacher
(74) *Attorney, Agent, or Firm* — Scully Scott Murphy & Presser, P.C.

(57) ABSTRACT

A medical instrument according to the present invention includes an end effector that fulfills a predetermined function, a motor unit that generates power for driving the end effector, a transmission member that is connected to the end effector and the motor unit so as to transmit the power to the end effector, a tension holding portion that has a tension generation portion and a tension pulley which is connected to the tension generation portion and which comes into contact with the transmission member the tension pulley being configured to move such that tension applied to the transmission member in a predetermined magnitude, and a switch that can fix a position of the tension pulley.

7 Claims, 7 Drawing Sheets

(51) Int. Cl.
    *B25J 3/00*         (2006.01)
    *B25J 9/06*         (2006.01)
    *B25J 9/10*         (2006.01)
    *B25J 15/00*       (2006.01)
    *A61B 34/00*      (2016.01)
    *A61B 34/30*      (2016.01)
    *A61B 1/005*      (2006.01)
    *A61B 17/29*      (2006.01)
    *A61B 90/00*      (2016.01)

(52) U.S. Cl.
    CPC ............ *B25J 9/065* (2013.01); *B25J 9/1045* (2013.01); *B25J 15/0019* (2013.01); *B25J 15/0028* (2013.01); *B25J 19/00* (2013.01); *A61B 1/0057* (2013.01); *A61B 17/29* (2013.01); *A61B 2017/2905* (2013.01); *A61B 2034/301* (2016.02); *A61B 2034/715* (2016.02); *A61B 2090/064* (2016.02)

(56) References Cited

U.S. PATENT DOCUMENTS

| | | | |
|---|---|---|---|
| 7,955,322 B2 * | 6/2011 | Devengenzo | A61B 1/00149 606/1 |
| 8,821,480 B2 * | 9/2014 | Burbank | A61B 34/71 606/1 |
| 2008/0308607 A1 | 12/2008 | Timm et al. | |
| 2010/0082041 A1 | 4/2010 | Prisco | |
| 2012/0046522 A1 | 2/2012 | Naito | |

FOREIGN PATENT DOCUMENTS

| | | |
|---|---|---|
| JP | 2002-200091 A | 7/2002 |
| JP | 2003-127076 A | 5/2003 |
| JP | 2009-028517 A | 2/2009 |
| JP | 2009-201607 A | 9/2009 |
| JP | 2010-268844 A | 12/2010 |
| JP | 2012-504016 A | 2/2012 |
| JP | 2012-100926 A | 5/2012 |
| WO | 2010/039387 A1 | 4/2010 |

OTHER PUBLICATIONS

Extended Supplementary European Search Report dated Feb. 5, 2018 in European Patent Application No. 15 81 8913.4.

* cited by examiner

MEDICAL INSTRUMENT AND ADJUSTMENT METHOD OF MEDICAL INSTRUMENT

This application is a continuation application based on a PCT International Application No. PCT/JP2015/066014, filed on Jun. 3, 2015, whose priority is claimed on Japanese Patent Application No. 2014-142574, filed on Jul. 10, 2014. The contents of both of the PCT International Application and the Japanese Patent Application are incorporated herein by reference.

BACKGROUND OF THE INVENTION

Field of the Invention

The present invention relates to a medical instrument, and more specifically relates to a medical instrument used by being inserted into a body of a patient, and an adjustment method of the medical instrument.

Description of Related Art

In the related art, a medical instrument has been widely used in which a distal end of an elongated insertion portion is provided with an end effector for observation or treatment. According to such a medical instrument, in order to bend the insertion portion or to drive the end effector, a drive force is transmitted to a distal end side in some cases. As a transmission member for transmitting the drive force, a wire such as a single wire or a stranded wire which is formed of a metal wire is generally used.

In a case where the insertion portion of the medical instrument is a flexible insertion portion, when the medical instrument is inserted into the body of the patient, the insertion portion may meander or may be bent. In such a case, a route length of the transmission member inserted into the insertion portion may vary. Accordingly, a magnitude of tension applied to the transmission member varies, compared to an initial state before the medical instrument is inserted into the body of the patient. As a result, if the transmission member becomes partially slack, responsivity with respect to the driving force by the transmission member becomes worse, thereby causing a problem in terms of accuracy in drive control or operability.

Regarding the problem, a slack adjustment device for an endoscope which can remove slack in an angle operating wire functioning as the transmission member is disclosed in the Japanese Unexamined Patent Application, First Publication No. H8-19511. According to the device disclosed in Japanese Unexamined Patent Application, First Publication No. H8-19511, a pulley having the angle operating wire hung thereon is attached to a slack removal member, and one end of the slack removal member is rotatably and axially supported by a casing. A user turns an adjusting screw by inserting a screwdriver into a hole disposed in the casing. In this manner, the user can remove the slack of the angle operating wire by rotating the slack removal member and moving the pulley.

SUMMARY OF THE INVENTION

According to a first aspect of the present invention, a medical instrument includes an end effector that fulfills a predetermined function, a power portion that generates power for driving the end effector, a transmission member that is connected to the end effector and the power portion so as to transmit the power to the end effector, a tension holding portion that has a tension generation portion and a movable portion which is connected to the tension generation portion and with which the transmission member comes into contact, the movable portion being configured to move such that tension applied to the transmission member is maintained at a predetermined magnitude, and a fixing portion that is capable of fixing a position of the movable portion.

According to a second aspect of the present invention, in the medical instrument according to the first aspect, the tension generation portion may be formed of an elastic member.

According to a third aspect of the present invention, in the medical instrument according to the first or second aspect, a plurality of the movable portions may be provided.

According to a fourth aspect of the present invention, in the medical instrument according to the third aspect, at least two of a plurality of the movable portions may be connected to each other in the tension generation portion.

According to a fifth aspect of the present invention, the medical instrument according to any one of the first to fourth aspects may further include an instrument unit that has the end effector and the transmission member, and an adapter that has the power portion and the fixing portion. The power portion and the transmission portion may be connected to each other while the movable portion may be fixed to be immovable by the fixing portion, when the instrument unit is mounted on the adapter.

According to a sixth aspect of the present invention, in the medical instrument according to any one of the first to fifth aspects, an annular power transmission route may be formed between the power portion and the end effector by the transmission member.

According to a seventh aspect of the present invention, there is provided an adjustment method of a medical instrument including an end effector that fulfills a predetermined function, a power portion that generates power for driving the end effector, and a transmission member that is connected to the end effector and the power portion so as to transmit the power to the end effector. The adjustment method of the medical instrument includes applying a predetermined magnitude of tension to the transmission member by using a tension holding portion that has a tension generation portion and a movable portion which is connected to the tension generation portion and which comes into contact with the transmission member, and fixing a position of the movable portion.

According to an eighth aspect of the present invention, the adjustment method of the medical instrument according to the seventh aspect may further include connecting the power portion and the transmission member to each other so that the power is capable of being transmitted until fixing a position of the movable portion.

DETAILED DESCRIPTION OF THE INVENTION

Hereinafter, a first embodiment according to the present invention will be described with reference to FIGS. 1 to 7. First of all, an example of a medical manipulator system which employs a medical instrument according to the present embodiment will be described.

Figure 1:
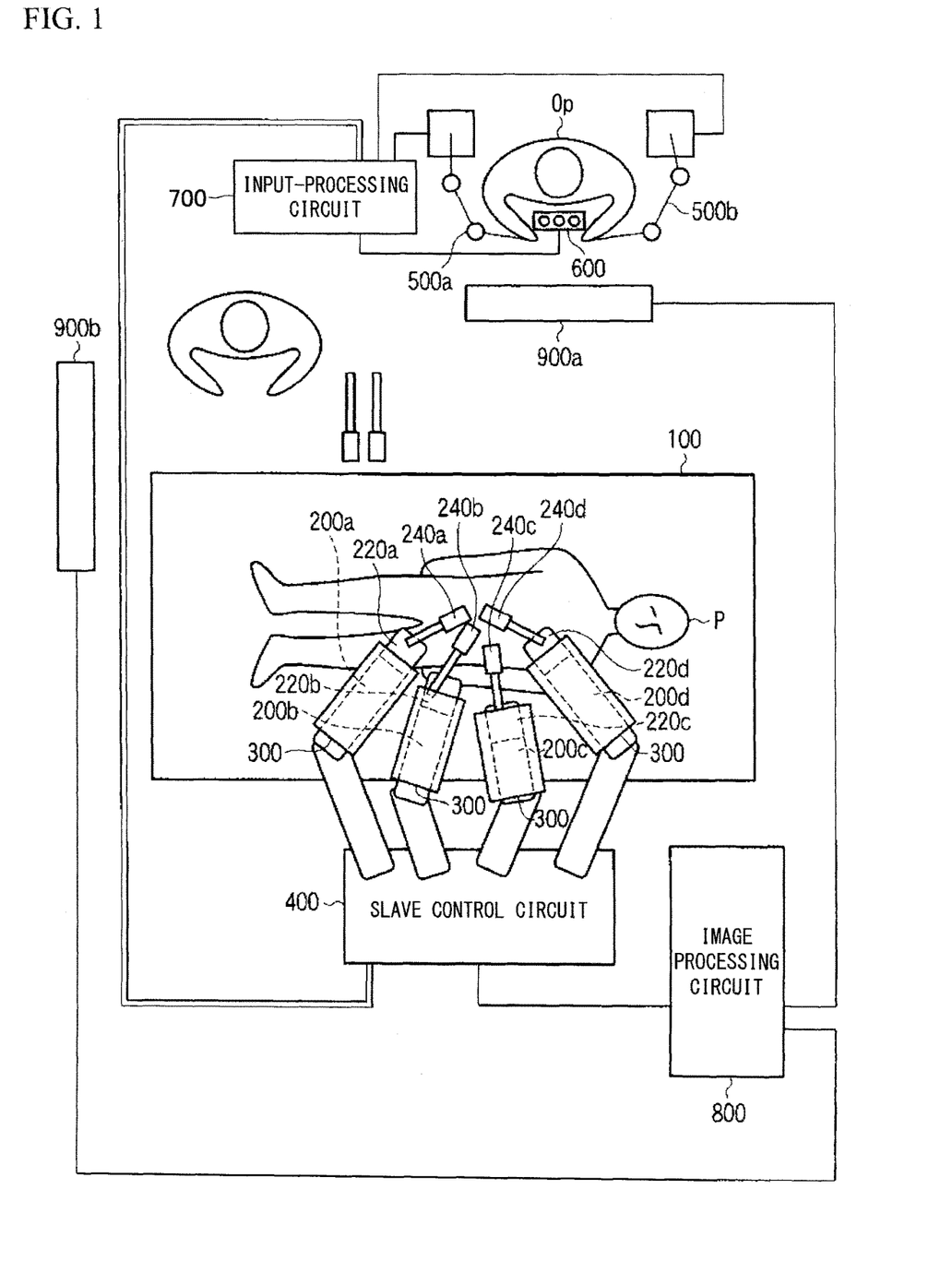
FIG. 1 is a view illustrating a medical manipulator system which employs a medical instrument according to the present invention.

FIG. 1 is a view illustrating an example of the medical manipulator system, and illustrates a master slave-type medical manipulator system. The master slave-type medical manipulator system represents a system which has two type arms including a master arm and a slave arm and which performs remote control on the slave arm so as to follow an operation of the master arm.

The medical manipulator system illustrated in FIG. 1 includes a surgical operation table 100, slave arms (manipulators) 200a to 200d, a slave control circuit 400, master arms 500a and 500b, an operation portion 600, an input processing circuit 700, an image processing circuit 800, and displays 900a and 900b.

The surgical operation table 100 is a table on which a patient P who is an observation/treatment target is placed. A plurality of the slave arms 200a, 200b, 200c, and 200d are disposed at the vicinity of the surgical operation table 100. The slave arms 200a to 200d may be installed in the surgical operation table 100.

The slave arms 200a, 200b, 200c, and 200d are configured to have a plurality of multi-degree of freedom joints, and the multi-degree of freedom joints are bent such that positions of instrument units and so on, which are mounted on a distal end side (side facing a body lumen of the patient P) of the slave arms 200a to 200d, are determined with respect to the patient P placed on the surgical operation table 100. The multi-degree of freedom joints are individually driven by a power portion (not illustrated). As the power portion, it is possible to use a motor (servo motor) having a servo mechanism including an incremental encoder or a speed reducer, for example. The operation control is performed by the slave control circuit 400.

In a case where the power portion of the slave arms 200a to 200d is driven, a drive amount of the power portion is detected by a position detector. A detection signal output from the position detector is input to the slave control circuit 400. The detection signal causes the slave control circuit 400 to detect the drive amount of the slave arms 200a to 200d.

Surgical power transmission adapters (hereinafter, simply referred to as "adapters") 220a, 220b, 220c, and 220d are interposed between the slave arms 200a, 200b, 200c, and 200d, and instrument units 240a, 240b, 240c, and 240d, and connect the slave arms 200a, 200b, 200c, and 200d, and the instrument units 240a, 240b, 240c, and 240d to each other. The adapters 220a to 220d have a plurality of power portions which generate power for driving the mounted instrument units 240a to 240d (details to be described later). Similarly to the power portion disposed in the slave arm, these power portions can employ the servo motor, for example. The operation control is performed by the slave control circuit 400. In this manner, the power generated in the power portion inside the adapter is transmitted to the corresponding instrument unit, thereby driving the respective instrument units.

For example, the slave control circuit 400 is configured to have a CPU or a memory. The slave control circuit 400 stores a predetermined program for controlling the slave arms 200a to 200d, and controls each operation of the slave arms 200a to 200d or the instrument units 240a to 240d in accordance with a control signal output from the input processing circuit 700. That is, based on the control signal output from the input processing circuit 700, the slave control circuit 400 specifies an operation target slave arm (or instrument unit) of the master arm operated by an operator Op, and calculates a drive amount required for allowing the specified slave arm to move corresponding to an operation amount of the master arm operated by the operator Op.

Then, the slave control circuit 400 controls an operation of the operation target slave arm of the master arm in accordance with the calculated drive amount. In this case, the slave control circuit 400 inputs a drive signal to the corresponding slave arm. In accordance with a detection signal input from the position detector of the power portion in response to the operation of the corresponding slave arm, the slave control circuit 400 controls a size or polarity of the drive signal so that the drive amount of the operation target slave arm reaches a target drive amount.

The master arms 500a and 500b are configured to include a plurality of link mechanisms. For example, a position detector such as an incremental encoder is disposed in each link configuring the link mechanism. The position detector detects an operation of each link, thereby causing the input processing circuit 700 to detect an operation amount of the master arms 500a and 500b.

The medical manipulator system illustrated in FIG. 1 operates the four slave arms by using the two master arms 500a and 500b. It is necessary to appropriately switch the operation target slave arms of the master arm. For example, this switching is performed by the operator Op operating the operation portion 600. As a matter of course, this switching becomes unnecessary if operation targets are caused to correspond one to one by matching the number of the master arms and the number of the slave arms.

The operation portion 600 has various operation members such as a switching button for switching the operation target slave arms of the master arms 500a and 500b, a scaling changing switch for changing an operation ratio between a master and a slave, and a foot switch for emergency system stopping. In a case where any one of the operation members configuring the operation portion 600 is operated by the operator Op, an operation signal in accordance with the operation of the corresponding operation member is input from the operation portion 600 to the input processing circuit 700.

The input processing circuit 700 analyzes the operation signal output from the master arms 500a and 500b and the operation signal output from the operation portion 600. In accordance with an analysis result of the operation signals, the input processing circuit 700 generates a control signal for controlling the medical manipulator system, and inputs the control signal to the slave control circuit 400.

The image processing circuit 800 performs various types of image processing for displaying an image signal input from the slave control circuit 400, and generates image data for being displayed on an operator's display 900a and an assistant's display 900b. For example, the operator's display 900a and the assistant's display 900b are configured to include a liquid crystal display, and display an image based on the image data generated in the image processing circuit 800 in accordance with an image signal acquired via an observation instrument.

In FIG. 1, the reference numeral 300 represents a drape for separating a region for performing sterilization treatment (clean region) and a region without performing the sterilization treatment (unclean region) from each other in the medical manipulator system according to the present embodiment.

According to the medical manipulator system configured as described above, if the operator Op operates the master arms 500a and 500b, the corresponding slave arm and the instrument unit attached to the slave arm are operated in response to the movement of the master arms 500a and 500b. In this manner, a desired manual technique can be used for the patient P.

Figure 2:
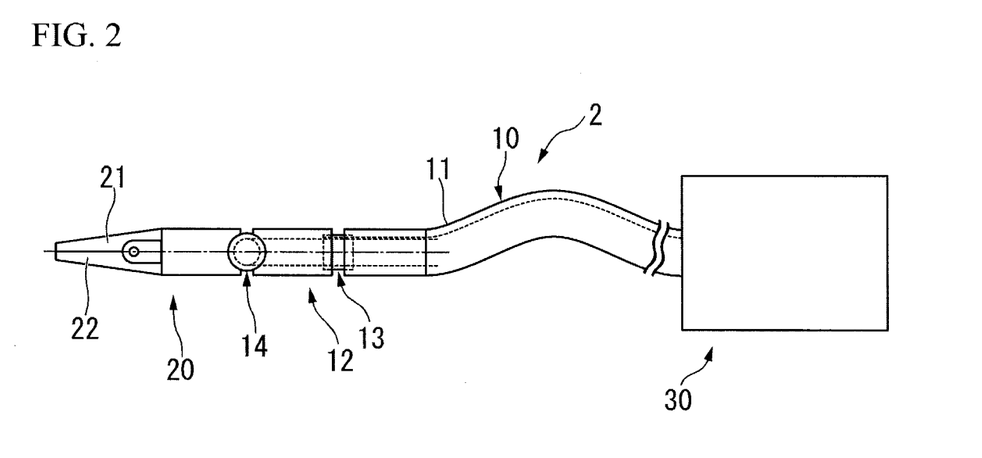
FIG. 2 is a view illustrating an instrument unit of a medical instrument according to a first embodiment of the present invention.
Figure 3:
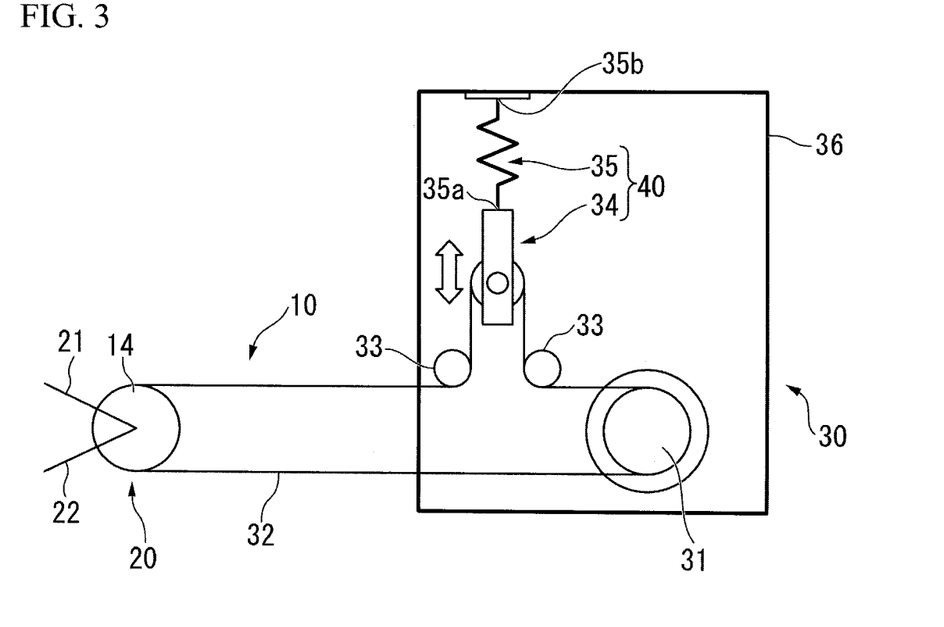
FIG. 3 is a view schematically illustrating a drive mechanism of the instrument unit according to the first embodiment of the present invention.

Next, the medical instrument according to the present embodiment will be described. The medical instrument is configured to include the above-described instrument unit and the corresponding adapter. FIG. 2 is a view schematically illustrating a brief configuration of an instrument unit 2 according to the present embodiment. As the above-described instrument unit (for example, 240d), the instrument unit 2 can be mounted on the adapter (for example, 220d). As illustrated in FIGS. 2 and 3, the instrument unit 2 includes an elongated insertion portion 10 which has a joint, an end effector 20 which is disposed in a distal portion of the insertion portion 10 and which fulfills a predetermined function, and a drive portion 30 for driving the joint of the insertion portion and the end effector.

The insertion portion 10 has a flexible portion 11 which is disposed on a proximal side and which is flexible, and a rigid portion 12 which is disposed on a distal end side from the flexible portion 11 and which is not flexible. A first joint 13 is disposed in the rigid portion 12.

The end effector 20 according to the present embodiment has a pair of jaws 21 and 22 and is connected to the insertion portion 10 via a second joint 14. The end effector 20 can change a direction of a pair of jaws 21 and 22 by driving the second joint 14. A pair of jaws 21 and 22 are opened or closed, thereby fulfilling a function as gripping forceps.

A structure of the drive portion 30 will be described later. The drive portion 30 is mounted on the adapter, thereby bringing each portion of the instrument unit 2 including the end effector 20 into a state where each portion can be driven.

FIG. 3 schematically illustrates a drive mechanism of the instrument unit 2. The drive portion 30 has a main pulley 31 connected to the power portion. The main pulley 31 and the second joint 14 are connected to each other so as to configure an annular power transmission route and so that a drive force can be transmitted therebetween in such a way that a linear transmission member 32 is fixed thereto while being wound one or more rounds. The transmission member 32 has flexibility that the transmission member 32 can be deformed to match the meandering or bent flexible portion 11 inside a patient's body and has rigidity that the transmission member 32 is not easily broken when driven. For example, the transmission member 32 can suitably employ a metal wire.

The power transmission route formed by the transmission member 32 is partially drawn out by an auxiliary pulley 33 in a direction away from the insertion portion 10 and the main pulley 31 inside the drive portion 30, and the power transmission route is partially hung on a tension pulley (movable portion) 34 such that the tension pulley 34 and the transmission member 32 are in contact with each other. A first end portion 35a of a tension generation member (tension generation portion) 35 is connected to the tension pulley 34, and a second end portion 35b is fixed to a housing 36 which accommodates each mechanism of the drive portion 30. As long as the tension generation member 35 can generate sufficient tension in view of a magnitude of initial tension to be applied to the transmission member 32, any configuration may be adopted, and for example, the tension generation member 35 can suitably employ a metal tension spring.

The tension pulley 34 and the tension generation member 35 function as the tension holding portion 40 which applies a predetermined magnitude of initial tension to the transmission member 32 and which holds the tension applied to the transmission member 32 so as to be substantially constant. That is, due to the tension generated by the tension generation member 35, the tension pulley 34 is biased so as to pull the hung transmission member 32 in the direction away from the insertion portion 10 and the main pulley 31. As a result, the tension pulley 34 is appropriately moved, thereby holding the magnitude of the tension applied to the transmission member 32 so as to be substantially constant.

Although not illustrated, the drive portion 30 further includes multiple sets of mechanisms having, the main pulley, the transmission member, and the tension holding portion. The first joint 13 and a pair of the jaws 21 and 22 are also driven using the similar mechanism.

Figure 4:
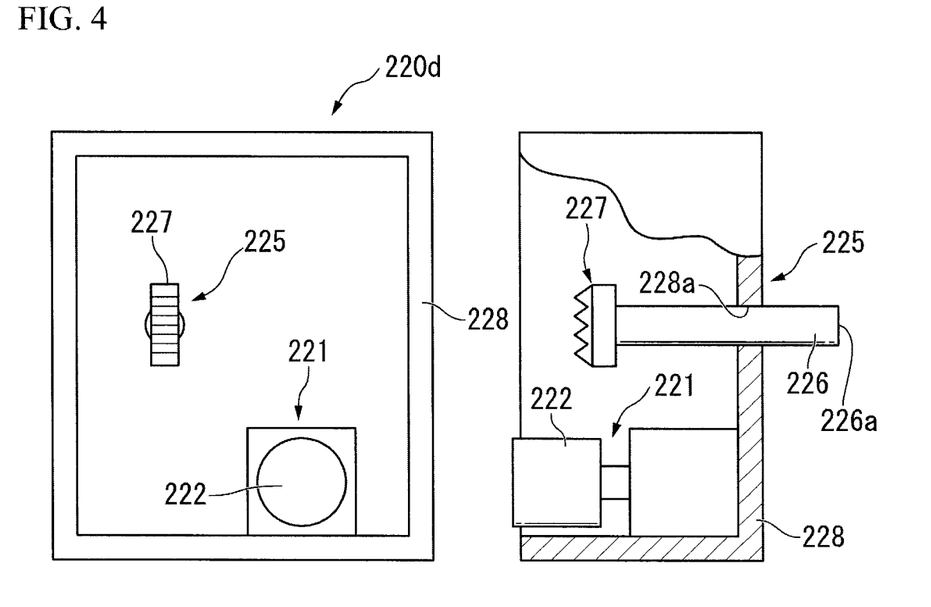
FIG. 4 is a view illustrating a structure of an adapter of the medical instrument according to the first embodiment of the present invention.

FIG. 4 schematically illustrates a structure of the adapter 220d. The left side in FIG. 4 shows a front view of the adapter 220d, and the right side shows a left side view of the adapter 220d, which are partially broken and illustrated for the sake of description. The adapter 220d includes a motor unit 221 serving as a power portion, a switch (fixing portion) 225 for switching on and off the function of the tension holding portion 40, and an exterior member 228 which accommodates the motor unit 221 and the switch 225. The exterior member 228 has a shape corresponding to the housing 36 of the instrument unit 2.

The motor unit 221 has a drive shaft portion 222 which can be connected to the main pulley 31. If the drive shaft portion 222 and the main pulley 31 are connected to each other, the drive shaft portion 222 is brought into a state where power generated in the motor unit 221 can be transmitted to the main pulley 31.

Figure 5:
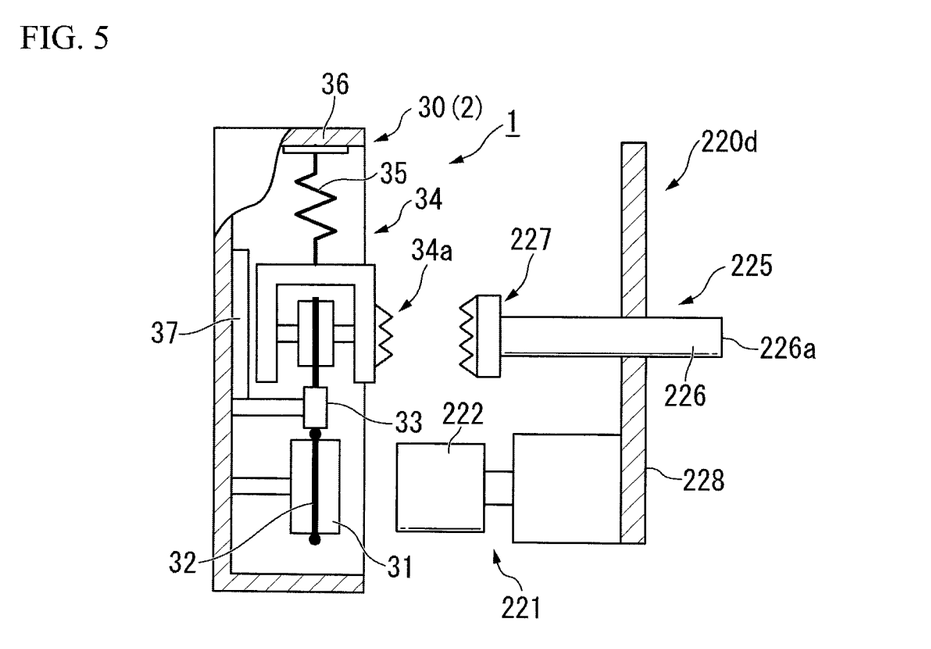
FIG. 5 is a view illustrating a state before the instrument unit according to the first embodiment of the present invention is attached to the adapter.

The switch 225 has a rod-shaped main body 226 and an engaging portion 227 disposed in a distal portion of the main body 226. The main body 226 is inserted into a through-hole 228a formed in the exterior member 228 so that the engaging portion 227 is located on an internal space side of the exterior member 228. The engaging portion 227 engages with an engaging-target portion 34a (refer to FIG. 5) disposed in the tension pulley 34, thereby holding a position of a rotary shaft of the tension pulley 34 so as to be immovable. As an example of the engaging portion and the engaging-target portion, FIGS. 4 and 5 illustrate a serrated structure. However, a specific aspect of the engaging portion and the engaging-target portion is not limited thereto, and for example, various known engagement structures such as a frictional engagement structure can be appropriately selected and used. A size in the movement direction of the tension pulley 34 or a size of a portion engaging with the engaging-target portion 34a is set in the engaging portion 227 so that the engaging portion 227 can engage with the engaging-target portion 34a even in a state where the tension pulley 34 is moved due to the holding tension applied to the transmission member 32.

The switch 225 is movable forward or rearward with respect to the exterior member 228 by operating a proximal portion 226a of the main body 226. The switch 225 has a structure for holding a position relative to the exterior member 228 and a structure for releasing the holding (both are not illustrated). For example, this structure can employ those which use a ratchet.

Although not illustrated, the adapter 220d is further provided with multiple sets of mechanisms having the motor unit and the switch so as to correspond to the first joint 13 and a pair of jaws 21 and 22.

An operation at the time of using the medical instrument 1 according to the present embodiment including the instrument unit 2 and the adapter 220d which are configured as described above, and an adjustment method of the medical instrument according to the present embodiment will be described.

As illustrated in FIG. 5, in a state before the instrument unit 2 is attached to the adapter 220d, due to tension generated in the tension generation member 35, the main pulley 31 is rotated, or the tension pulley 34 is moved, thereby causing the tension holding portion 40 to apply a predetermined magnitude of initial tension to the transmission member 32. If the instrument unit 2 is inserted into a patient's body, the flexible portion 11 meanders or is bent inside the body, and the shape of the flexible portion 11 may be changed. As a result, a route length of the transmission member may also be changed, and the transmission member 32 may be partially slack. Even in this case, if the movement of the main pulley 31 and the tension pulley 34 is not limited, the tension pulley 34 of the tension holding portion 40 is appropriately moved, and a magnitude of the tension applied to the transmission member 32 is held substantially constant, thereby removing the slack (first step in the adjustment method of the medical instrument).

Figure 6:
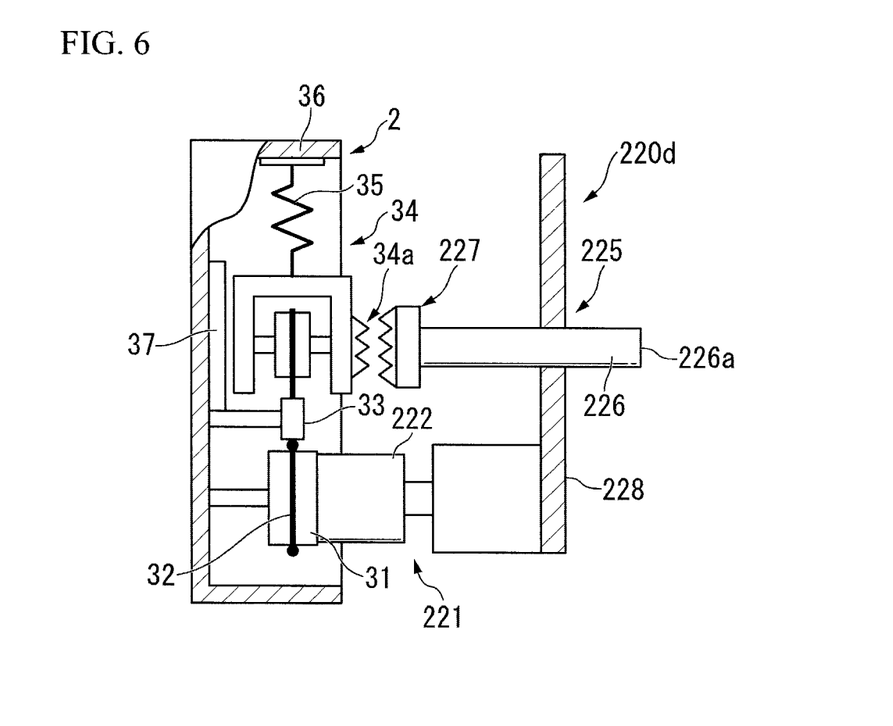
FIG. 6 is a view illustrating a state where a motor unit and a main pulley are connected to each other.
Figure 7:
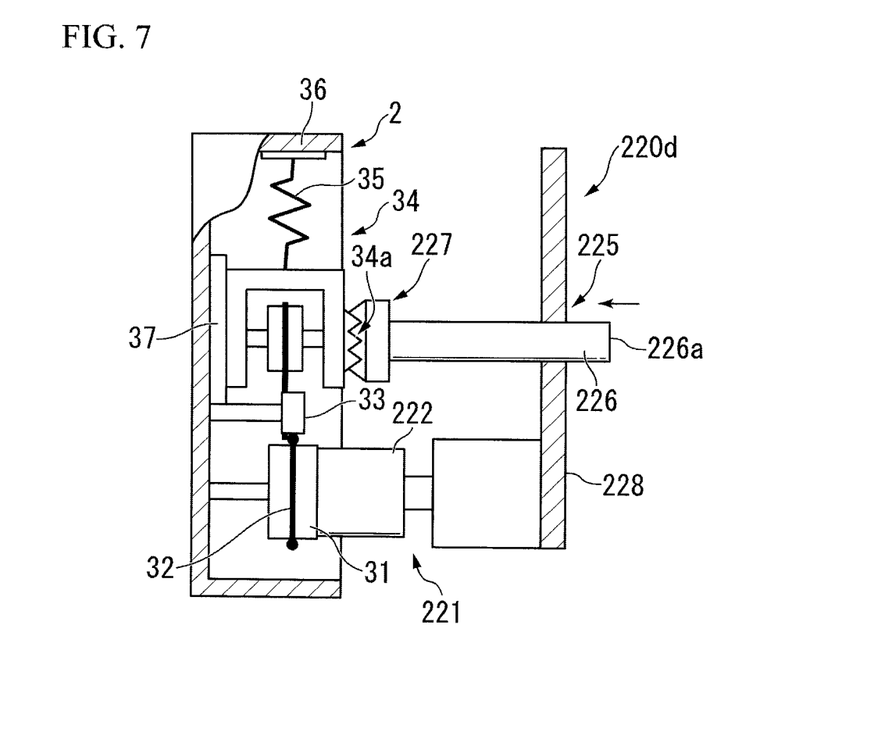
FIG. 7 is a view illustrating a state where a tension pulley is fixed.

When the instrument unit 2 in which the tension applied to the transmission member 32 is held substantially constant in the first step is attached to the adapter 220d, the housing 36 of the instrument unit 2 and the exterior member 228 are fitted together so as to face each other. In this manner, as illustrated in FIG. 6, the main pulley 31 and the motor unit 221, and the engaging-target portion 34a of the tension pulley 34 and the engaging portion 227 of the switch 225 are positioned so as to face each other, and a drive shaft portion 222 of the motor unit 221 and the main pulley 31 are connected to each other. As a result, the motor unit 221 and the transmission member 32 are connected to each other so that power generated in the motor unit 221 can be transmitted therebetween (second step). FIGS. 5 to 7 illustrate a partially excluded view of the exterior member 228 in order to clearly show the inside of the adapter 220d.

When the switch 225 is in an initial state, even if the drive shaft portion 222 and the main pulley 31 are connected to each other as illustrated in FIG. 6, the engaging portion 227 and the engaging-target portion 34a do not engage with each other. Therefore, in a state illustrated in FIG. 6, free pivoting of the main pulley 31 is restricted by the motor unit 221. However, the main pulley 31 can be moved without fixing a position of the rotary shaft of the tension pulley 34.

If the motor unit 221 is driven in a state illustrated in FIG. 6, the main pulley 31 pivots.

The pivoting of the main pulley 31 is transmitted to the second joint 14 via the transmission member 32, thereby drive the second joint 14. However, if the rotary shaft of the tension pulley 34 is moved when driven, there is a possibility that the movement of the transmission member 32 may become unstable. Therefore, a user operates the switch 225 before the motor unit 221 is driven to cause the rotary shaft of the tension pulley 34 to be fixed such that the rotary shaft of the tension pulley is immovable with respect to the insertion portion 10 and the main pulley 31, and the pivoting of the tension pulley 34 is not hindered. That is, the user pushes the proximal portion 226a of the main body 226 such that the engaging portion 227 and the engaging-target portion 34a are engaged with each other as illustrated in FIG. 7, and the user pushes the tension pulley 34 against a fixing member 37 attached to the housing 36 (fixing step). It is preferable that the fixing member 37 is formed of a material which can generate a sufficient frictional force between the tension pulley 34 and the fixing member 37. For example, the fixing member 37 can be formed of rubber.

When the motor unit 221 is driven after the position of the rotary shaft of the tension pulley 34 is fixed, the second joint 14 can be driven in a state where the movement of the transmission member 32 is stable. At this moment, the pivoting of the tension pulley 34 is not hindered such that a force amount required for driving the transmission member 32 is not substantially changed. Also, since the transmission member 32 is driven only when the motor unit 221 is driven, a magnitude of the tension applied to the transmission member 32 is not substantially changed after the fixing step is performed.

In a case where the instrument unit 2 is exchanged, the switch 225 is returned to an initial position, and the housing 36 is detached from the exterior member 228. In the instrument unit 2 detached from the adapter 220d, the tension holding portion 40 is appropriately operated, thereby holding the magnitude of the tension applied to the transmission member 32.

As described above, in the medical instrument 1 according to the present embodiment including the instrument unit 2 and the adapter 220d, the tension holding portion 40 is disposed in the transmission member 32 arranged between the main pulley 31 and the second joint 14 of the end effector 20. Therefore, even if a user does not perform active action such as turning a screw with a screwdriver, a magnitude of the tension applied to the transmission member 32 is held substantially equal to that of initial tension. Accordingly, it is not necessary to perform a complicated operation in order to maintain or adjust the tension applied to the transmission member 32. The tension is preferably prevented from becoming excessively great or excessively small.

Even if the instrument unit 2 is used in any arrangement configuration, since the magnitude of the tension applied to the transmission member 32 is held substantially equal to that of the initial tension, an environment for using the medical instrument may not be limited.

Furthermore, in a case where the instrument unit 2 is stored for a long time, in a case where the instrument unit 2 receives an impact during transportation, or in a case where the insertion portion 10 or the transmission member 32 expands or contracts after sterilization treatment is performed, the tension is held by the tension holding portion 40. Accordingly, when the instrument unit 2 starts to be used, the magnitude of the tension applied to the transmission member 32 is held satisfactorily.

Since the adapter 220d is provided with the switch 225 which can fix the position of the rotary shaft of the tension pulley 34 so as to be immovable, the end effector 20 can be suitably driven by fixing the tension pulley 34, after the main pulley 31 and the motor unit 221 are connected to each other in a state where proper tension is applied to the transmission member 32. As a result, it is possible to prevent a tension variation amount from being added to the tension of the transmission member 32, and it is possible to suitably prevent controllability from becoming poor.

Furthermore, the transmission member 32 causes the annular power transmission route to be formed between the motor unit 221 and the end effector 20. Therefore, even if any section of the power transmission route becomes slack, the slack can be suitably removed by the movement of the tension pulley 34. Therefore, a position for disposing the tension holding portion 40 can be more freely selected, and the drive portion 30 can be easily configured.

In the present embodiment, an example has been described in which the switch 225 is operated so as to fix the tension pulley 34 after the motor unit 221 and the main pulley 31 are first connected to each other and the power portion and the transmission member 32 are connected to each other. However, the instrument unit and the adapter may be configured so that the movement of the tension pulley 34 is stopped concurrently or substantially concurrently when the motor unit 221 and the main pulley 31 are connected to each other. In such a configuration, for example, the initial position of the engaging portion 227 of the switch 225 may be removed, or the switch 225 may be driven so as to approach the tension pulley 34 in synchronization with the approach between the main pulley 31 and the motor unit 221.

It is preferable that the tension holding portion 40 is operable until the main pulley 31 and the motor unit 221 are connected to each other. Accordingly, timing for fixing the tension pulley 34 may be set to be concurrent with or slightly later than when the motor unit 221 and the main pulley 31 are connected to each other.

In order to connect the motor unit and the transmission member to each other, drive force transmission may be switched on or off. A configuration may not be necessarily adopted in which both of these are physically separated from each other. Therefore, a configuration may be adopted in which the drive force transmission can be switched on or off by a clutch while both of these are always physically connected to each other.

According to the configuration in the present embodiment, a force obtained by deducting the gravitational force applied to the tension pulley 34 from the tension generated by the tension generation member 35 is applied to the transmission member 32. Accordingly, in view of this point, a magnitude of the tension to be generated by the tension generation member 35 may be set.

Next, a second embodiment according to the present invention will be described with reference to FIGS. 8 and 9.

A different point between the present embodiment and the first embodiment is a configuration of the tension holding portion. In the following description, the same reference numerals will be given to configurations which are common to those which are previously described, and thus, repeated description will be omitted.

Figure 8:
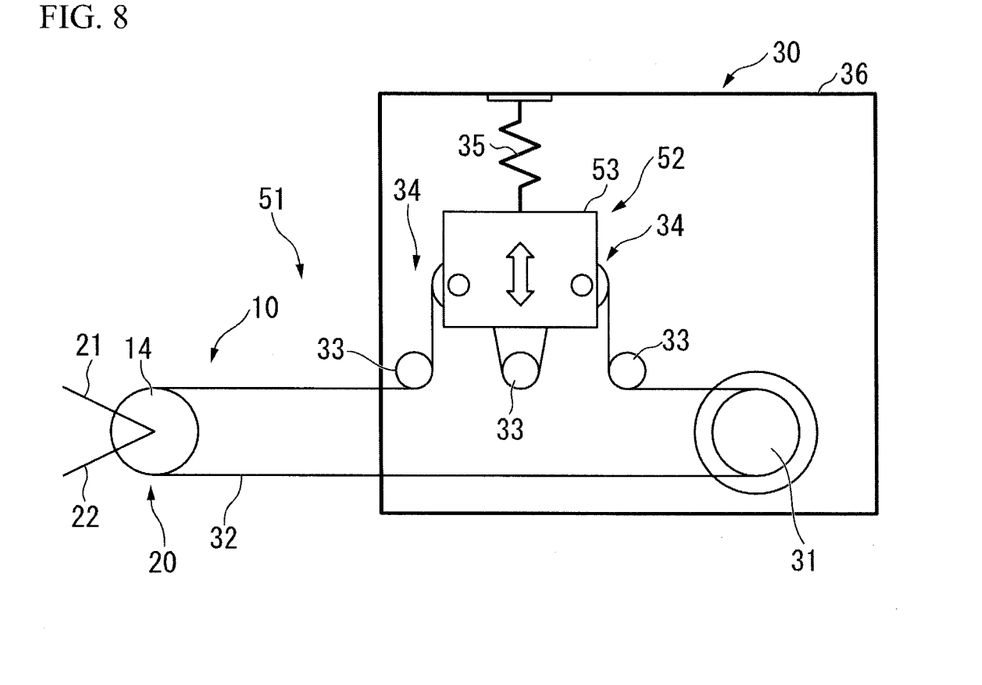
FIG. 8 is a view schematically illustrating a drive mechanism of an instrument unit according to a second embodiment of the present invention.
Figure 9:
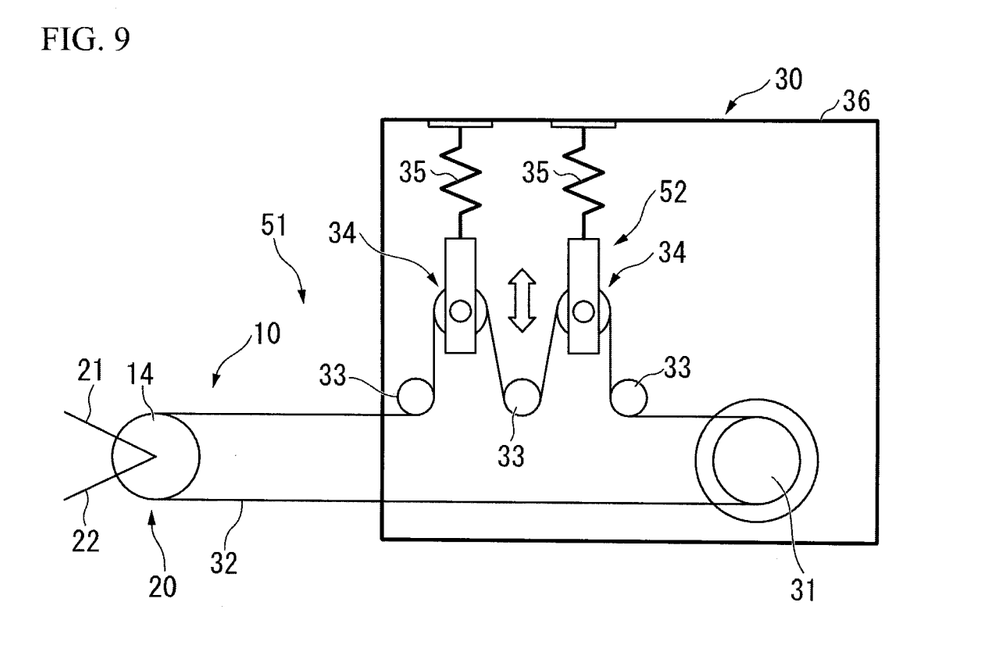
FIG. 9 is a view schematically illustrating a drive mechanism according to a modification example of the instrument unit in the second embodiment of the present invention.

FIG. 8 is a side view schematically illustrating an instrument unit 51 according to the present embodiment. A tension holding portion 52 has two tension pulleys 34, and the transmission member 32 is also hung on the two tension pulleys 34. The two tension pulleys 34 are axially supported by a common support portion 53 so as to be pivotable. An end portion of the tension generation member 35 is connected to the support portion 53.

In the medical instrument according to the present embodiment which has the instrument unit 51, similarly to the first embodiment, it is also not necessary to perform the complicated operation. A magnitude of the tension applied to the transmission member can be held substantially equal to that of the initial tension.

The tension holding portion 52 has a plurality of the tension pulleys 34. Accordingly, a movement range of the tension pulley 34 moved due to the tension adjustment can be minimized, compared to that according to the first embodiment. As in the present embodiment, in a case where the tension holding portion 52 has the two tension pulleys 34, the movement range of the tension pulley 34 which is required for removing a certain amount of slack is ½ of that according to the first embodiment. In this manner, the medical instrument can be configured to be miniaturized by configuring the drive portion 30 to be more compact.

In the present embodiment, the number of the tension pulleys can be appropriately set, and three or more may be provided. As in a modification example illustrated in FIG. 9, a plurality of the tension pulleys 34 may be independently arranged so as to be movable, and the tension generation member 35 may be connected to the respective tension pulleys 34.

Next, a third embodiment according to the present invention will be described with reference to FIG. 10. A different point between the present embodiment and the above-described embodiments is a configuration of the tension holding portion.

Figure 10:
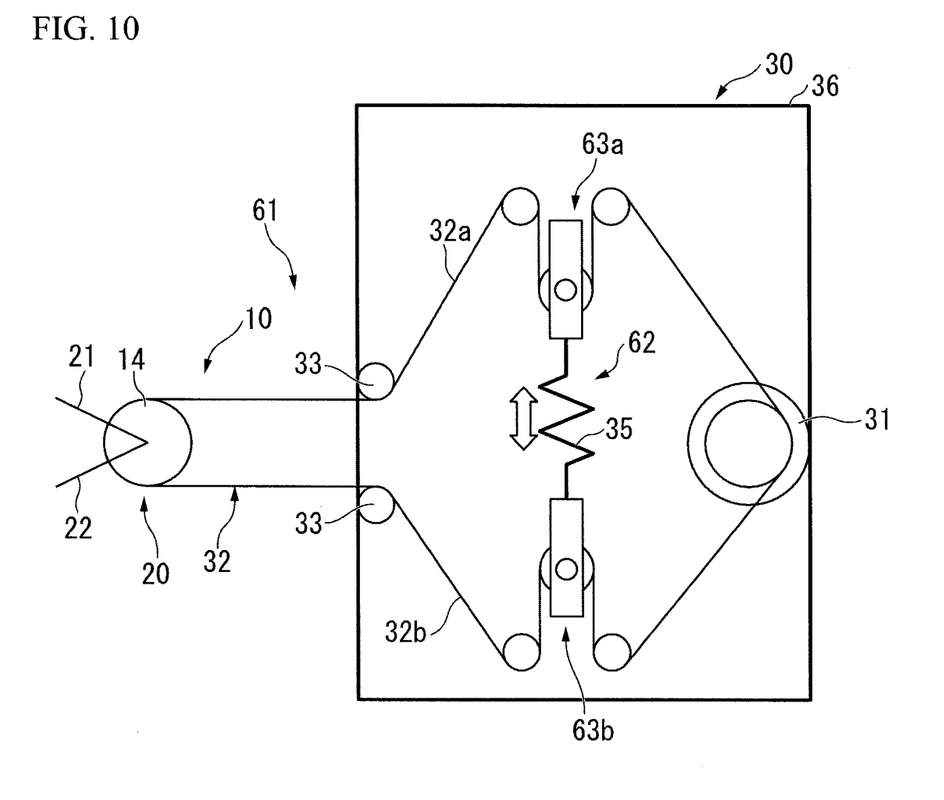
FIG. 10 is a view schematically illustrating a drive mechanism of an instrument unit according to a third embodiment of the present invention.

FIG. 10 is a side view schematically illustrating an instrument unit 61 according to the present embodiment. A distance in the annular transmission member 32 increases inside the drive portion 30, compared to the inside of the insertion portion 10.

A tension holding portion 62 according to the present embodiment has two tension pulleys, similarly to the second embodiment. In contrast, one tension pulley 63a is hung on a first region 32a on the upper side of the transmission member 32, and the other tension pulley 63b is hung on a second region 32b on the lower side of the transmission member 32. The two tension pulleys 63a and 63b are connected to each other by the tension generation member 35.

In the medical instrument according to the present embodiment which has the instrument unit 61, similarly to the above-described embodiments, it is also not necessary to perform the complicated operation. A magnitude of the tension applied to the transmission member 32 can be held substantially equal to that of the initial tension.

Since the tension pulley 63a is arranged in the first region 32a and the tension pulley 63b is arranged in the second region 32b, wherein the first region 32a and the second region 32b are located on both sides of the second joint 14, the slack occurring in the first region 32a and the second region 32b is suitably removed by the tension pulleys 63a and 63b respectively. As a result, even when frictional forces applied to the transmission member 32 are different from each other between the first region 32a and the second region 32b due to a shape of the flexible portion 11, the slack is prevented from remaining in one region. Therefore, it is possible to more suitably hold the tension applied to the transmission member 32.

Furthermore, the two tension pulley 63a and 63b are connected to the tension generation member 35. In this manner, the weights of the tension pulleys can be compensated with each other. As a result, it becomes less necessary to consider the weight of the tension pulley in setting the tension generation member. Therefore, the initial tension is easily set.

The respective embodiments according to the present invention have been described. However, the technical scope of the present invention is not limited to the above-described embodiments. Within the scope not departing from the gist of the present invention, the combination of the configuration elements can be changed, various modifications can be added to the respective configuration elements, or the configuration elements can be deleted.

For example, a guide for regulating the movement direction of the tension holding portion may be disposed in the housing. In this case, without depending on a posture of the drive portion, the movement of the tension holding portion can be stabilized.

In the above-described respective embodiments, an example has been described in which the tension generation member pulls the transmission member in the direction away from the insertion portion and the main pulley. Alternatively, a configuration may be adopted in which a pushing spring is used as the tension generation member so as to push the transmission member in contact in the direction away from the insertion portion and the main pulley. If the friction is less generated between the transmission member and the movable portion, the movable portion may not necessarily be the pulley.

Figure 11:
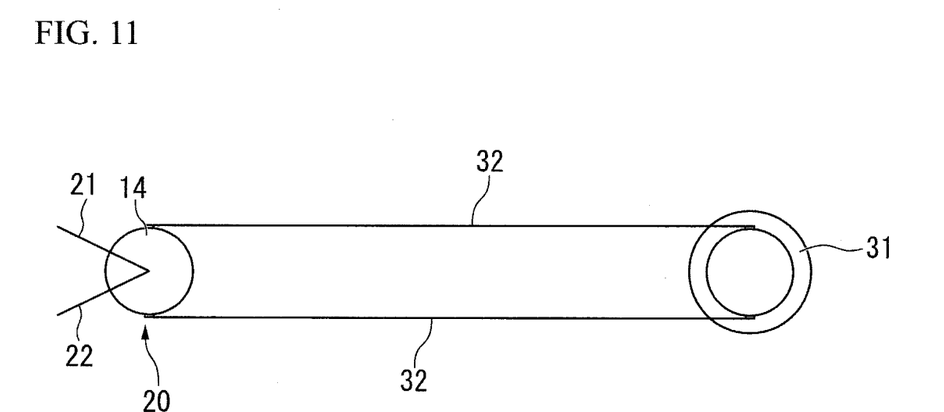
FIG. 11 is a view illustrating another example of a transmission member in the medical instrument according to the first embodiment of the present invention.

In the present invention, the power transmission route may not necessarily be formed in the annular shape. In a schematic view of a modification example illustrated in FIG. 11, two linear transmission members 32 are arranged between the main pulley 31 and the second joint 14. Since each end portion of the transmission members are respectively fixed to the main pulley 31 and the second joint 14, although it seems like that the transmission member forms a loop, the two transmission member are not connected to each other, accordingly, the power transmission route has no annular shape. Even according to this configuration, substantially the same advantageous effect can be obtained by disposing the tension holding portion in at least one (preferably, both sides) of the transmission members 32 which are located between the main pulley 31 and the end effector 20.

Even in a case where the power transmission route is formed in the annular shape, a configuration is not limited to the above-described aspect. For example, the annular transmission member may be engaged using friction by being wound around between the power portion and the end effector.

Figure 12:
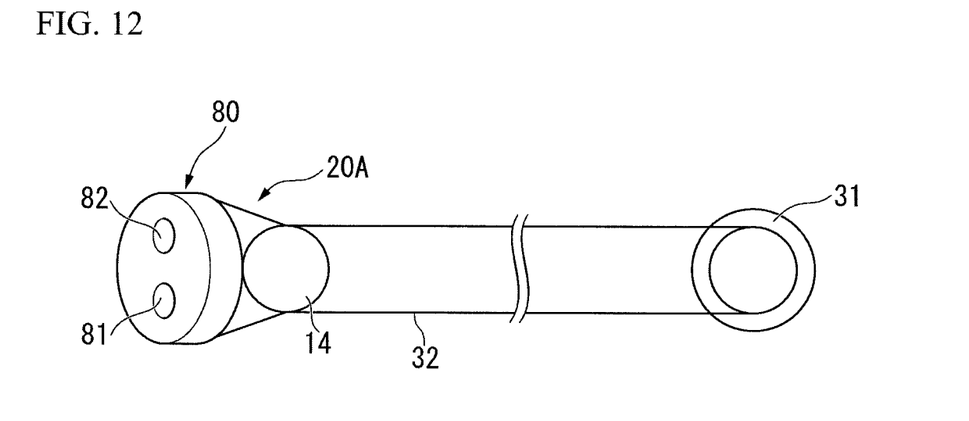
FIG. 12 is a view illustrating a modification example of an end effector in the medical instrument according to the first embodiment of the present invention.
Figure 13:
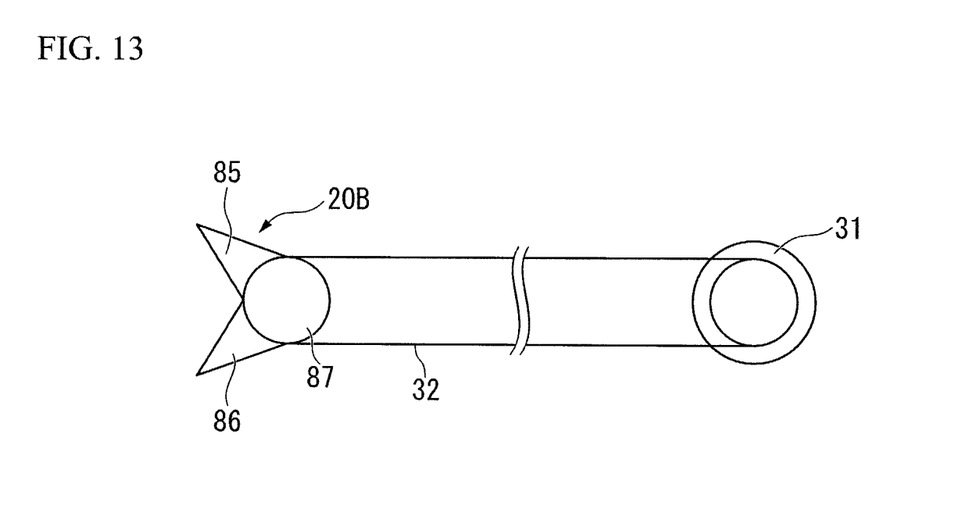
FIG. 13 is a view illustrating a modification example of the end effector in the medical instrument according to the first embodiment of the present invention.

The end effector according to the present invention includes various types. For example, as in a modification example illustrated in FIG. 12, an end effector 20A may be employed in which an observation unit 80 having an observation portion 81 having an image sensor element and an illumination portion 82 having a light source is attached to the second joint 14. Even in a case of the end effector functioning as gripping forceps, as in an end effector 20B according to a modification example illustrated in FIG. 13, a configuration may be adopted in which a pair of jaws 85 and 86 are driven by the transmission member 32. Although not illustrated in FIG. 13, the jaw 86 is attached to another opening/closing pulley separate from an opening/closing pulley 87 having the jaw 85 attached thereto. Another main pulley and transmission member are connected to the separate opening/closing pulley. According to this configuration, the jaws 85 and 86 can be respectively pivoted. The pivoting operations of a pair of the jaws are caused to cooperate with each other, thereby enabling the jaws to function as the gripping forceps. In addition to these configurations, the end effector according to the present invention also includes a bending mechanism having multiple joint rings or bent pieces, and a joint disposed in the insertion portion.

Furthermore, in the above-described respective embodiments, an example has been described in which the insertion portion has the flexible portion. However, the flexible portion is not essential in the medical instrument according to the present invention. Even if the medical instrument includes a so-called rigid insertion portion having no flexible portion, in a case where the transmission member is flexible, an advantageous effect can be obtained. However, in a case where the insertion portion includes the flexible portion, the route length of the transmission member is likely to be changed. Accordingly, a greater advantageous effect according to the present invention is obtained.

The medical instrument according to the present invention is not limited to those which include the electric power portion such as the motor. Therefore, the present invention can also be applied to a case where a user's operation input serves as a direct power source, for example, a manual medical instrument which includes a dial knob as the power portion. In this case, as long as the user does not perform the operation input, power is not transmitted to the transmission member. Accordingly, the dial knob serving as the power portion may be always connected to the transmission member.

The number of joints disposed in the insertion portion or a free degree of the medical instrument realized by the number of joints may be appropriately set.

The respective embodiments according to the present invention have been described. However, the technical scope of the present invention is not limited to the above-described embodiments. Within the scope not departing from the gist of the present invention, the combination of the configuration elements in the respective embodiments can be changed, various modifications can be added to the respective configuration elements, or the configuration elements can be deleted. The present invention is not limited by the above description.

The embodiments of the invention have been described above with reference to the drawings, but specific structures of the invention are not limited to the embodiments and may include various modifications without departing from the scope of the invention. The invention is not limited to the above-mentioned embodiments and is limited only by the accompanying claims.

What is claimed is:

1. A medical instrument comprising:
an instrument unit comprising:
  an end effector fulfilling a predetermined function; and
  a wire;
an adapter comprising:
  a motor for generating power to drive the end effector; and
  a fixing portion; and
a tension holding portion comprising:
  a pulley movable in translation along a direction and with which the wire comes into contact; and
  a spring for biasing the pulley;
wherein the tension holding portion being configured to maintain a tension applied to the wire at a predetermined magnitude due to a movement of the pulley in the direction;
the wire is connected to both the end effector and the motor so as to transmit the power generated by the motor to the end effector;
the fixing portion is configured to fix a position of the pulley; and
when the instrument unit is mounted on the adapter, the motor and the wire are connected with each other while the pulley is fixed by the fixing portion so as to be immovable in the direction.

2. The medical instrument according to claim 1, wherein the pulley comprises a plurality of pulleys.

3. The medical instrument according to claim 2, wherein at least two of the plurality of pulleys are biased by one of the spring or two or more springs.

4. The medical instrument according to claim 1, wherein an annular power transmission route is formed between the motor and the end effector by the wire.

5. An adjustment method of a medical instrument including an instrument unit having an end effector that fulfills a predetermined function and a wire, an adapter having a motor that generates power to drive the end effector and a fixing portion, the wire being connected to the end effector and the motor so as to transmit the power to the end effector, the adjustment method comprising:
applying a tension having a predetermined magnitude to the wire by a tension holding portion that has a spring and a pulley biased by the spring and with which the wire comes into contact; and
fixing a position of the pulley in translation,
wherein when the instrument unit is mounted on the adapter, the motor and the wire are connected with each other while the pulley is fixed by the fixing portion so as to be immovable in translation.

6. The adjustment method of a medical instrument according to claim 5, further comprising:
prior to the step of fixing the position of the pulley, connecting the motor and the wire to each other so that the power is capable of being transmitted.

7. The adjustment method of a medical instrument according to claim 5, wherein slack in the wire is removed by applying the tension having the predetermined magnitude to the wire.

* * * * *